(12) United States Patent
Heckerman et al.

(10) Patent No.: US 12,366,505 B1
(45) Date of Patent: Jul. 22, 2025

(54) ENRICHMENT OF SURGICAL SPECIMENS FOR TUMOR TISSUE

(71) Applicant: Amazon Technologies, Inc., Reno, NV (US)

(72) Inventors: David Heckerman, Bellevue, WA (US); Frank Wilhelm Schmitz, Seattle, WA (US); Michael Vogelsong, Seattle, WA (US)

(73) Assignee: Amazon Technologies, Inc., Reno, NV (US)

( * ) Notice: Subject to any disclaimer, the term of this patent is extended or adjusted under 35 U.S.C. 154(b) by 770 days.

(21) Appl. No.: 17/519,655

(22) Filed: Nov. 5, 2021

Related U.S. Application Data

(60) Provisional application No. 63/110,627, filed on Nov. 6, 2020.

(51) Int. Cl.
G01N 1/30 (2006.01)
C12Q 1/6869 (2018.01)
G06N 3/08 (2023.01)

(52) U.S. Cl.
CPC ............. *G01N 1/30* (2013.01); *C12Q 1/6869* (2013.01); *G06N 3/08* (2013.01); *G01N 2001/302* (2013.01); *G01N 2001/305* (2013.01)

(58) Field of Classification Search
None
See application file for complete search history.

(56) References Cited

U.S. PATENT DOCUMENTS

| | | | |
|---|---|---|---|
| 2016/0278746 A1* | 9/2016 | Hancu | A61B 5/4312 |
| 2017/0309063 A1* | 10/2017 | Wang | G06T 19/003 |
| 2018/0140197 A1* | 5/2018 | Wang | A61B 5/0077 |

* cited by examiner

*Primary Examiner* — Blaine Lankford
(74) *Attorney, Agent, or Firm* — Hogan Lovells US LLP

(57) ABSTRACT

Disclosed herein is a method for determining tumor margins relative to non-tumorous tissue using a deep-learning platform. Also disclosed herein are methods for removing a tumor from a tumor biopsy.

23 Claims, 4 Drawing Sheets

ENRICHMENT OF SURGICAL SPECIMENS FOR TUMOR TISSUE

The present application claims the benefit of U.S. Provisional Application No. 63/110,627 filed on Nov. 6, 2020, the entire contents of which are incorporated herein by reference.

1. BACKGROUND

Cancer is a leading cause of death worldwide accounting for 1 in 4 of all deaths. Siegel et al., CA: A Cancer Journal for Clinicians, 68:7-30 (2018). There were 18.1 million new cancer cases and 9.6 million cancer-related deaths in 2018. Bray et al., CA: A Cancer Journal for Clinicians, 68(6):394-424. Immunotherapeutic treatments, such as personalized cancer vaccines, require accurate and complete characterization of tumors in order to fully contextualize. A key consideration for techniques that are employed to characterize tumors, such as single-cell RNA sequencing, is to include as little normal tissue as possible. Failure to do can lead to lead to decreased sensitivity, accuracy, and efficiency.

Tumor biopsies are typically examined by pathologists to demarcate tumor margins. This procedure involves analyzing the gross resection specimen macroscopically and representative histopathology sections of the tissue through microscopy. With this method, it is challenging to evaluate the entire tumor margin as large amounts of histologic tissue sections need to be examined to fully evaluate the tumor specimen. As an additional complexity, cancers have irregular contours and ill-defined margins leading to inconspicuous borders with surrounding tissue. Such techniques are prone to error because subtle differences between the tumor and non-tumorous tissue often evades the naked eye. As such, conventional techniques are prone to including non-tumorous tissue in the tumor margins. Indeed, it has been found that when using conventional techniques about 50% of samples include non-tumorous material.

Machine-learning platforms have been applied in the field of oncology for various modalities, for example radiological imaging, histopathological staining, diagnosis, staging, and classification of cancer (e.g., melanoma, prostate cancer). While machine-learning platforms appear to be a promising tool, major challenges exist. Machine-learning platforms tend to have limited interpretability, are prone to overfitting, and do not necessarily show consistent performance when analyzing data not used during training. Accordingly, there is an unmet need for new techniques, particularly those associated with personalized cancer therapy, that can accurately and efficiently determine a tumor margin and distinguish tumor tissue from non-tumorous tissue.

2. SUMMARY

This disclosure relates to new methods for accurately and efficiently determining a tumor margin of a biopsy relative to non-tumor margins relative to non-tumorous tissue using a deep-learning platform. The methods can further be used for removing non-tumorous tissue from a tissue biopsy. The methods described herein are used to enrich a tumor from a tumor biopsy such that the removed tumor has a higher ratio of tumor to non-tumor tissue than tumors removed from biopsies using conventional methods. This is advantageous for techniques that are used in characterizing tumors, such as single-cell RNA sequencing, because a higher amount of tumor relative to non-tumorous tissue leads to less dilution of the tumor and greater accuracy. This enables characterization of tumors with high sensitivity and accuracy.

The methods described herein first comprise preparing the tumor biopsy. The tumor biopsy can be prepared by staining the tumor biopsy, fixing the tumor biopsy, or freezing the tumor biopsy. The tumor biopsy is preferably a fresh tumor biopsy. Next, the tumor biopsy is optionally registered with a registration indicator. The registration indicator may be an ink or a plurality of inks. The inks employed can each be a different color. Following, the tumor biopsy is sectioned into one or more sections. Preferably, the tumor biopsy is sectioned at least about twice. The sectioned tumor biopsy can then be fixed or stained. Preferable fixing techniques include freezing or using formalin. The tumor biopsy can be stained with one or more tissue inks. Typically, the one or more tissue inks are each a different color. Alternatively, the sectioned tumor biopsy can be stained with hematoxylin and eosin stain.

Following fixing or staining of the sectioned tumor biopsy, a deep-learning platform is applied to each section of the tumor biopsy to determine the tumor margin relative to non-tumorous tissue in the tumor biopsy. The deep-learning platform distinguishes tumor tissue from non-tumorous tissue. The deep-learning platform can be a convolutional neural network or an artificial neural network. Lastly, the tumor margins are interpolated from the tumor biopsy sections across the tumor biopsy to determine the tumor margin. An exemplary interpolation method is spline interpolation. Once the tumor margin has been determined, the non-tumorous tissue can be removed from the tumor biopsy. The tumor biopsy will have a higher ratio of tumor to non-tumor tissue. The enriched tumor sample is advantageous for techniques that are used to characterize tumors, such as single-cell RNA sequencing or single-cell DNA sequencing.

The methods described herein can be suitable for any tumor. Exemplary tumors include, but are not limited to, melanoma or skin tumor, breast cancer tumor, ovarian cancer tumor, prostate cancer tumor, kidney cancer tumor, liver cancer tumor, gastric cancer tumor, colon cancer tumor, testicular cancer tumor, head and neck cancer tumor, pancreatic cancer tumor, brain cancer tumor, B-cell lymphoma tumor, acute myelogenous leukemia tumor, chronic myelogenous leukemia tumor, chronic lymphocytic leukemia tumor, T-cell lymphocytic leukemia tumor, bladder cancer tumor, or lung cancer tumor. Preferably, the tumor is a melanoma tumor, a breast cancer tumor, or a lung cancer tumor.

3. BRIEF DESCRIPTION OF THE DRAWINGS

4. DETAILED DESCRIPTION

Figure 1:
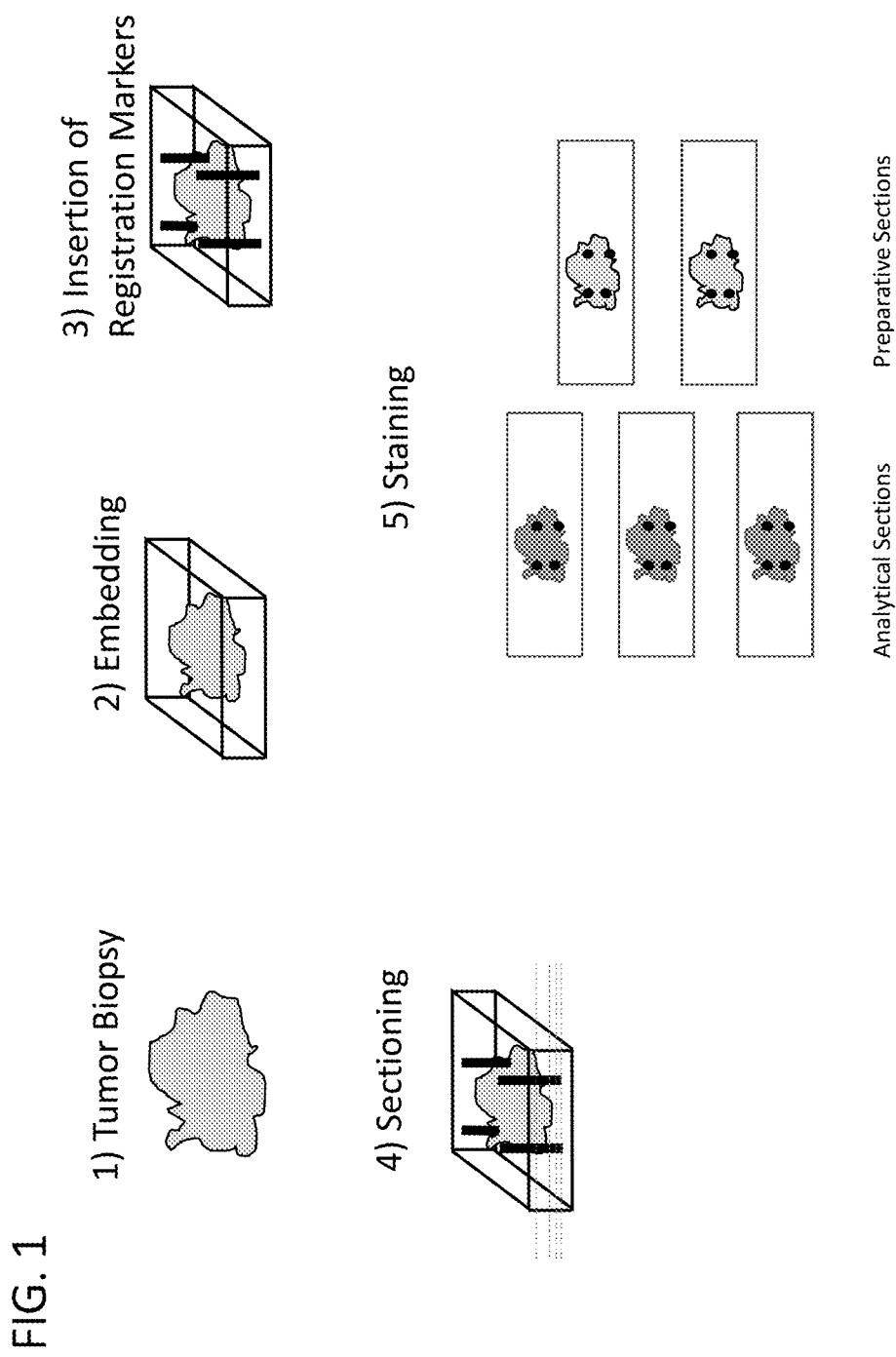
FIG. 1 is a schematic diagram depicting the steps for tumor sample enrichment that comprises a tumor biopsy, embedding, inserting a registration marker, sectioning and staining.

Current methods and techniques for determining tumor margins are unreliable, inaccurate, expensive, and time consuming. Deep-learning models face major challenges, particularly with respect to interpretability and accurate performance. Further, deep-learning has not been used as a tool for determining the tumor margins of a tumor biopsy in order to enrich a tumor biopsy up until now.

This disclosure relates to new methods for accurately determining tumor margins relative to non-tumorous tissue using a deep-learning platform. These methods can further be used for removing non-tumorous tissue from a tumor biopsy. The methods described herein are used to enrich a tumor from a tumor biopsy such that the removed tumor has a higher ratio of tumor to non-tumor tissue than tumors removed from biopsies using conventional methods. This is advantageous for techniques that are used in characterizing tumors, such as single-cell RNA sequencing, because a higher amount of tumor relative to non-tumorous tissue leads to less dilution of the tumor and greater accuracy. This enables characterization of tumors with high sensitivity and accuracy. The inventor's approach begins with preparing a tumor biopsy. To prepare the tumor biopsy, the tumor biopsy can be stained or preferably, frozen. Without being bound by theory, frozen samples are preferable for sequencing. Optionally, the tumor biopsy can be registered with a registration indicator, such as an ink or wax. The registration indicator can be applied to the surface of the tumor biopsy or injected into the tumor biopsy. A column can be used to guide the registration indicator into the interior of the tumor biopsy. The registration indicator can be used to understand how the tumor coordinates need to be transferred and can be useful for interpolation. Once the tumor biopsy has been prepared and optionally registered, the tumor biopsy can then be sectioned. The tumor biopsy can be sectioned into one or more sections. For example, the tumor biopsy can be sectioned into two sections or the tumor biopsy can be sectioned into three sections. Next, the sectioned tumor biopsy is fixed (e.g., in formalin) and stained (e.g., hematoxylin and eosin stain). Following the staining and sectioning, a deep-learning platform is applied to determine the tumor margin relative to non-tumorous tissue in the tumor biopsy. The deep-learning platform distinguishes tumor tissue from non-tumorous tissue. The deep-learning platform determines the tumor margin relative to non-tumorous tissue based on a training set and validation set, given by examples. The deep-learning platform then generalizes from the given examples to learn the ability to locate and identify tumor margins on the tumor biopsy. Once the deep-learning platform has determined the tumor margin relative to the non-tumorous tissue in the tumor biopsy, the tumor margins from the sectioned biopsy can be interpolated. Interpolation reconstructs the tumor margins for a three-dimensional (3-D) tumor biopsy from the two-dimensional sectioned tumor biopsy. This enables the margins of the tumor to be visualized. For example, the deep-learning platform can generate an output image. Once the tumor margin has been determined, the non-tumorous tissue can be removed from the tumor biopsy. The tumor biopsy will have a higher ratio of tumor to non-tumor tissue. The enriched tumor sample is advantageous for techniques that are used to characterize tumors, such as single-cell RNA sequencing or single-cell DNA sequencing.

All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present disclosure. When a range of values is expressed, it includes embodiments using any particular value within the range. Further, reference to values stated in ranges includes each value within that range. All ranges are inclusive of their endpoints and combinable. When values are expressed as approximations, by use of the antecedent "about," it will be understood that the particular value forms another embodiment. Reference to a particular numerical value includes at least that particular value, unless the context clearly dictates otherwise. The use of "or" will mean "and/or" unless the specific context of its use dictates otherwise.

Various terms relating to aspects of the description are used throughout the specification and claims. Such terms are to be given their ordinary meaning in the art unless otherwise indicated. Other specifically defined terms are to be construed in a manner consistent with the definitions provided herein. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular forms "a," "an," and "the" include plural forms unless the context clearly indicates otherwise. The terms "include," "such as," and the like are intended to convey inclusion without limitation, unless otherwise specifically indicated.

Unless otherwise indicated, the terms "at least," "less than," and "about," or similar terms preceding a series of elements or a range are to be understood to refer to every element in the series or range. Those skilled in the art will recognize, or be able to ascertain using no more than routine experimentation, many equivalents to the specific embodiments of the invention described herein. Such equivalents are intended to be encompassed by the following claims.

The term "ink" as used herein refers to any coloring element that can be applied to a tumor biopsy, such as dye, paint, fluorescent marker, plastic (rod), isotypes, fluorescent spheres, Quantum dots (Qdot™) and stains.

The term "neural network" as used herein refers to a machine-learning model for classification or regression consisting of multiple linear transformations or non-linear transformations followed by element-wise nonlinearities typically trained via stochastic gradient descent and back-propagation.

The term "subject" herein refers to any animal, such as any mammal, including but not limited to, humans, non-human primates, rodents, and the like. In some embodiments, the mammal is a mouse. In some embodiments, the mammal is a human.

The term "tumor margin" herein refers to the edge, border, or boundary of a tumor.

Additional description of the methods and guidance for the practice of the methods are provided herein.

The methods disclosed herein comprise determining a tumor margin in a specimen derived from a tumor biopsy. The methods described herein are applicable to any tumor biopsy. As such, the invention should not be limited to the tumors described herein as the method is well suited for use with any tumorous tissue. The tumor biopsy can be obtained from human or non-human subjects. Preferentially, the tumor biopsy is obtained from a human. The tumor biopsy can be obtained from a variety of biological sources that comprise cancerous tumors. The source of a tumor biopsy can be a solid tissue sample, such as a tumor tissue biopsy. Tissue biopsy samples may be biopsies from, e.g., lung, prostate, colon, skin, breast tissue, or lymph nodes.

The tumor biopsy described herein can be obtained directly from a subject, derived from a subject, or derived from samples obtained from a subject, such as cultured cells derived from a biological fluid or tissue sample. The tumor biopsy can be a fresh sample. The fresh sample can be fixed after removal from the subject with any known fixatives (e.g. formalin, Zenker's fixative, or B-5 fixative). The tumor biopsy can also be archived samples, such as frozen samples, cryopreserved samples, of cells obtained directed from a subject or of cells derived from cells obtained from a subject. Preferably, the tumor biopsy obtained from a subject is a fresh tumor biopsy.

The tumor biopsy can be obtained from a subject by any means including, but not limited to, needle aspirate, scraping, shaving, surgical incision, venipuncture, excision biopsy, incision biopsy, shave/tangential biopsy, punch biopsy or curetting or other means known in the art. A tumor biopsy is a preferred method for obtaining the tumor. The tumor biopsy can be obtained from any cancerous site, for example, a primary tumor or a secondary tumor. A tumor biopsy from a primary tumor is generally preferred. Those skilled in the art will recognize other suitable techniques for obtaining tumor biopsies.

The tumor biopsy can be obtained from the subject in a single procedure. The tumor biopsy can be obtained from the subject repeatedly over a period of time. For example, the tumor biopsy can be obtained once a day, once a week, monthly, biannually, or annually. The tumor biopsy can be obtained from the same tumor or from different tumors.

The methods disclosed herein can be used for any suitable tumor. Illustrative suitable cancer tumors include, for example, tumors caused by adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, Wilms tumor, and chronic lymphocytic leukemia.

Preferably, the tumor is a melanoma tumor, breast cancer tumor, ovarian cancer tumor, prostate cancer tumor, kidney cancer tumor, gastric cancer tumor, colon cancer tumor, testicular cancer tumor, head and neck cancer tumor, pancreatic cancer tumor, brain cancer tumor, B-cell lymphoma tumor, acute myelogenous leukemia tumor, chronic myelogenous leukemia tumor, chronic lymphocytic leukemia tumor, T-cell lymphocytic leukemia tumor, bladder cancer tumor, or lung cancer tumor. Of particular interest are melanoma tumors, breast cancer tumors, lung cancer tumors, and bladder cancer tumors.

The cancer can be a solid tumor or a liquid tumor. The methods disclosed herein are preferably suited for solid tumors. The tumor can be a primary tumor (e.g., a tumor that is at the original site where the tumor first arose) or one or many a metastases.

The first step of the method for determining the tumor margin includes preparing the tumor biopsy. Those skilled in the art will be familiar with techniques that can be employed to prepare a tumor biopsy. Any such technique can be employed to prepare the tumor biopsy. For example, the tumor biopsy can be prepared by fixing or staining the tumor biopsy. Further details on fixation and staining are provided below. Preferably, the tumor biopsy is fixed. The preferred fixing method is freezing. Without being bound by theory, freezing is more advantageous for tumor characterization techniques, such as single-cell RNA sequencing or single-cell DNA sequencing.

The tumor biopsy can optionally be registered with a registration indicator. The registration indicator can adhere securely to the tumor biopsy tissue. The registration indicator can be useful for interpolating the tumor margins from the tumor sections across the tumor biopsy. Exemplary registration indicators include, but are not limited to, ink and wax, plastic, punch holes. The registration indicator marks the surface of the tumor biopsy. Alternatively, the registration indicator can be injected into the tumor biopsy. In some instances, the registration indicator can be injected into the tumor biopsy using a column. The column can be used to guide the registration indicator to interior sections of the tumor biopsy.

Depending on the type of tumor, different colored inks can be used on a tumor biopsy to designate the exterior surface margin or other specific margins, particular anatomical features, or particular areas of the tumor biopsy.

The surface of the tumor biopsy can be marked using a tissue marking ink. Tissue marking ink can be applied using any suitable applicator known to those of skill in the art, for example, a paint brush, a cotton swab, or a stick applicator. The tissue marking ink preferably dries quickly when applied to the tissue and maintains the fidelity of the markings without smearing or migrating on the tissue surface.

Commercially available tissue marking inks can be employed. Commercially available kits are generally well known and commonly employed by those of skill in the art. Exemplary commercially available tissue marking inks include, but are not limited to, Original 7 Dye Color Kit®, CDI's Ink Aid™, MarginMarker™, India ink, Shandon™, BioVitrum, acrylic paints or gelatin. Other inks can include eosin powder, orange G 6, fevicryl hobby colors, aniline, light green, methylene blue, alcian blue, mercurochrome, camlin permanent markers, eraz-ex, gelatin with added colors, and camel acrylic special waterproof ink. Another type of tissue marking ink that may be employed is a tattoo ink or Chinese traditional ink. In other embodiments, a fluorescent ink can be employed.

The tumor biopsy can be stained with one or more tissue marking inks. In some instances, a single tissue marking ink can be used. In other cases, a plurality of tissue marking inks can be used. For example, one tissue marking ink, two tissue marking inks, three tissue marking inks, four tissue marking inks, five tissue marking inks, six tissue marking inks, seven tissue marking inks, eight tissue marking inks, nine tissue marking inks, ten tissue marking inks, eleven tissue marking inks, twelve tissue marking inks, thirteen tissue marking inks, fourteen tissue marking inks, fifteen tissue marking inks, or more than fifteen tissue marking inks, can be used to stain the tumor biopsy.

The color of the ink employed can be blue, green, yellow, white, pink, purple, red, brown, silver, gold, bronze, black, or orange. Other colors can also be employed, if desired. Some colors may be preferable based on the results. For example, black, green and blue inks may provide excellent results. In contrast, other colors may not provide a clear delineation. In addition, different colors can be employed depending on the type of tumor. For example, a breast cancer tumor maybe better examined using yellow, red, and blue inks. Whereas a melanoma tumor may be better examined using purple, yellow, and green inks. The actual color of ink employed can vary. In instances in which a plurality of inks and/or stains are employed, each ink/or stain can be a different color.

In embodiments, the registration indicator can be a wax, such as paraffin wax, bee wax, or molten wax.

Next, the tumor biopsy is sectioned. The tumor biopsy can be sectioned using any known technique, for example the tumor biopsy can be placed in a cryostat while a microtome slices the tumor into multiple pieces. The tumor biopsy can be sectioned at least about once, at least about twice, at least about three times, at least about four times, at least about five times, at least about six times, at least about seven times, at least about eight times, at least about nine times, at least about ten times, or more. Preferably, the tumor biopsy is sectioned two or three times.

The tumor biopsy can be sectioned into any size desired. For example, the tumor biopsy can be sectioned into slices that are approximately about 1 µm thick, approximately 2 µm thick, approximately 3 µm thick, approximately 4 µm thick, approximately 5 µm thick, approximately 6 µm thick, approximately 7 µm thick, approximately 8 µm thick, approximately 9 µm thick, approximately 10 µm thick, approximately 15 µm, approximately 20 µm, approximately 30 µm thick, approximately 40 µm thick, approximately 50 µm thick, approximately 60 µm thick, approximately 70 µm thick, approximately 80 µm thick, approximately 90 µm thick, approximately 100 µm thick, approximately 200 µm thick, approximately 300 µm thick, approximately 400 µm thick, approximately 500 µm thick, approximately 600 µm thick, approximately 700 µm thick, approximately 800 µm thick, approximately 900 µm thick or larger.

The tumor biopsy can be sectioned into slices that are approximately about 1 mm thick, approximately about 2 mm thick, approximately about 3 mm thick, approximately about 4 mm thick, approximately about 5 mm thick, approximately about 6 mm thick, approximately about 7 mm thick, approximately about 8 mm thick, approximately about 9 mm thick, approximately about 10 mm thick, approximately about 15 mm thick, approximately about 20 mm thick, or larger.

In embodiments, the tumor biopsy can be sectioned into one or more sizes. For instance, the tumor biopsy may be sectioned into one, two, three, four, five, six, seven, eight, nine, or ten different biopsy sizes.

The sectioned tumor biopsy is then fixed and stained. The sectioned tumor biopsy can be fixed by freezing or using a fixative. Freezing is the preferred fixing method. The sectioned tumor biopsy can be frozen at a temperature of at least 0° C., at least −5° C., at least −10° C., at least −15° C., at least −20° C., at least −40° C., at least −50° C., at least −60° C., at least −70° C., at least −80° C., at least −100° C. or lower. Alternatively, the tumor biopsy can be frozen in liquid nitrogen, cryopreserved, or in isopentane cooled to −80° C. Another method of freezing is to permeate or perfuse the tissue with glycerine, polyethylene glycol, glycerol, optimal curing temperature compound or sucrose solutions. Those of skill in the art will understand appropriate methods for freezing tumor biopsy material.

Fixative refers to a compound used to preserve biological specimens. The type of fixative applied depends on the type of tumor biopsy and/or the type of tumor. There are generally three types of fixative processes: heat fixation, immersion, and perfusion. A typical fixation process applied in the methods disclosed herein is immersion. The fixative can be an aldehyde, an alcohol, an oxidizing agent, mercurial, picrates, or a hepes-glutamic acid buffer-mediated organic solvent protection effect (HOPE).

Fixatives include, but are not limited to, formalin, formaldehyde, para-formaldehyde, glutaraldehyde, methanol, ethanol, acetone, osmium tetroxide, potassium dichromate, chromic acid, potassium permanganate, B-5 fixative, Zenker's fixative, Weigners, Bouin's solution, Hollande's, Green-Fix, formal calcium, formal saline, zinc formalin, Helly's fixative, UPM, Cymol, Grendre's solution, Clarke's solution, Carnoy's solution, methacarn, formal acetic alcohol, Excell-Plus, FineFix, RCL2, HOPE, Glyo-Fixx, and Cellblock. Alternatively, the sectioned tumor biopsy can be fixed with formalin, but one of skill in the art will appreciate any number of fixatives may be used. Preferably, the sectioned tumor biopsy is fixed with formalin and embedded in paraffin (referred to as formalin-fixed paraffin-embedded (FFPE) fixation).

The sectioned tumor biopsy is then stained. Without being bound by theory, the sectioned tumor biopsy is stained to enhance the contrast of the sectioned tumor biopsy. Any number of stains can be applied to the sectioned tumor biopsy. Exemplary stains include, but are not limited to, acridine orange, Bismarck brow, carmine, coomassie blue, cresyl violet, crystal violet, DAPI, eosin, ethidium bromide, acid fuchsin, haemoxylin, Hoechst stains, iodine, malachite green, methyl green, methylene blue, neutral red, nile blue, nile red, osmium tetroxide, propidium iodine, rhodamine, and safranine. A preferred stain employed in the methods disclosed herein is hematoxylin and eosin stain.

The methods disclosed herein further comprise applying a deep-learning platform to determine the tumor margin relative to non-tumorous tissue. The deep-learning platform distinguishes tumor tissue from non-tumorous tissue. A deep-learning platform obtains the tumor margin based on a training set provided by examples. Approaches to generate training data include asking the pathologist to draw the margins or editing the margins estimated with earlier models. The deep-learning platform then generalizes from the provided training set examples to learn the ability to determine tumor margins on a tumor biopsy.

The deep-learning platform employed herein determines the tumor margin relative to non-tumorous tissue based on a validation data set. The validation data set can be images of tumor margins across one or more forms of tumors. In embodiments, the validation set number is at least 10 to 100,000,000 biopsy specimens. The validation data set number can be at least 50 to 100,000,000 biopsy specimens, at least 100 to 100,000,000 biopsy specimens, at least 200 to 100,000,000 biopsy specimens, at least 300 to 100,000,000 biopsy specimens, at least 400 to 100,000,000 biopsy specimens, at least 500 to 100,000,000 biopsy specimens, at least 600 to 100,000,000 biopsy specimens, at least 700 to 700,000,000 biopsy specimens, at least 800 to 100,000,000 biopsy specimens, at least 900 to 100,000,000 biopsy specimens, at least 1,000 to 100,000,000 biopsy specimens, at least 2,000 to 100,000,000 biopsy specimens, at least 3,000 to 100,000,000 biopsy specimens, at least 4,000 to 100,000,000 biopsy specimens, at least 5,000 to 100,000,000 biopsy specimens, at least 6,000 to 100,000,000 biopsy specimens, at least 7,000 to 100,000,000 biopsy specimens, at least 8,000 to 100,000,000 biopsy specimens, at least 9,000 to 100,000,000 biopsy specimens, at least 10,000 to 100,000,000 biopsy specimens, at least 50,000 to 100,000,000 biopsy specimens, or at least 100,000 to 100,000,000 biopsy specimens. In embodiments, the validation data set number can be at least 10 biopsy specimens, at least 20 biopsy specimens, at least 30 biopsy specimens, at least 40 biopsy specimens, at least 50 biopsy specimens, at least 100 biopsy specimens, at least 200 biopsy specimens, at least 300 biopsy specimens, at least 400 biopsy specimens, at least 500 biopsy specimens, at least 600 biopsy specimens, at least 700 biopsy specimens, at least 800 biopsy specimens, at least 900 biopsy specimens, at least 1,000 biopsy specimens, at least 2,000 biopsy specimens, at least 3,000 biopsy specimens, at least 4,000 biopsy specimens, at least 5,000 biopsy specimens, at least 6,000 biopsy specimens, at least 7,000 biopsy specimens, at least 8,000 biopsy specimens, at least 9,000 biopsy specimens, at least 10,000 biopsy specimens, at least 15,000 biopsy specimens, at least 20,000 biopsy specimens, at least 30,000 biopsy specimens, at least 40,000 biopsy specimens, at least 50,000 biopsy specimens, at least 60,000 biopsy specimens, at least 70,000 biopsy specimens, at least 80,000 biopsy specimens, at least 90,000 biopsy specimens, at least 100,000 biopsy specimens, at least 200,000 biopsy specimens, at least 300,000 biopsy specimens, at least 400,000 biopsy specimens, at least 500,000 biopsy specimens, at least 600,000 biopsy specimens, at least 700,000 biopsy specimens, at least 800,000 biopsy specimens, at least 900,000 biopsy specimens, at least 100,000,000 biopsy specimens, or more.

The validation data set can be based across one or more tumor types. For example, the validation set number can be based on at least 1 tumor type, at least 2 tumor types, at least 3 tumor types, at least 4 tumor types, at least 5 tumor types, at least 6 tumor types, at least 7 tumor types, at least 8 tumor types, at least 9 tumor types, at least 10 tumor types, at least 11 tumor types, at least 12 tumor types, at least 13 tumor types, at least 14 tumor types, at least 15 tumor types, at least 16 tumor types, at least 17 tumor types, at least 18 tumor types, at least 19 tumor types, at least 20 tumor types, at least 30 tumor types, at least 40 tumor types, at least 50 tumor types, at least 60 tumor types, at least 70 tumor types, at least 80 tumor types, at least 90 tumor types, at least 100 tumor types, or more. The validation data set can be based on tumor biopsy specimens from one or more subjects, or a combination thereof. The validation data set can be based on tumor biopsy specimens at any stage. The validation data set can be based on tumor biopsy specimens of any grade. For example, the tumor biopsy specimen may be grade 0, grade 1, grade 2, grade 3, or grade 4. The validation data set can be based on tumor biopsy specimens of any size. For example, at least 0.1 mm, at least 0.25 mm, at least 0.5 mm, at least 0.7 mm, at least 0.9 mm, at least 1.0 mm, at least 1.5 mm, at least 2 mm, at least 3 mm, at least 4 mm, at least 5 mm, at least 10 mm, or greater.

In some instances, the validation data set can be obtained from open-source datasets. For example, the Cancer Imaging Archive (http://www.cancerimagingarchive.net) provides image datasets with appropriate reference labels for cancers, or The Cancer Genome Atlas Program.

Deep-learning is a sub-field of machine-learning, where algorithms learn features directly from data for prediction and classification. The deep-learning model can be an artificial neural network. The construction of neural networks is based on a stack of neurons composed of activation functions and parameters to extract and integrate features from the images and establish a model that captures the complex relationship between tumorous tissue and non-tumorous tissue. The neural network can be a deep learning model with convolutional neural network. The convolutional neural network platform can employ the steps of preprocessing tumor biopsy images, generating cancerous margins from non-cancerous regions from the tumor biopsy images, training a convolutional neural network to distinguish from tumor margins and the non-cancerous regions, selecting thresholds for analysis from the model prediction, and testing the model on both local and external testing sets.

This is achieved based on local connections with weights followed by a form of pooling, which results in more efficient detection of translation invariant features. Each convolutional layer of a convolutional neural network is a set of triplets of convolution, non-linear, and pooling layers that enable the model to learn linear, and pooling layers that enable the model to learn, extract and enhance implicit features of an image. The triplet layer as a whole is called the convolutional layer. When stacked together, the first layers act like a feature filter such as an edge enhancer and allow the convolutional layer to extract local features, which are passed to deeper convolutional layers, which act like increasingly more global feature extractors. A convolutional neural network comprises one or more convolutional layers. Further, the one or more convolutional layers are followed by one or more fully connected layers as in a standard multilayer neural network. Each convolutional layer contains a set of feature maps, or filters, that extract features from a region of units using a convolution. Then an additive bias is applied, and the result is passed through a sigmoid function. In a convolutional neural network, the convolution layers are applied on 2D feature maps to compute spatial features.

In the pooling layers, a region of the previous layer is connected to a unit in the current layer, reducing the dimension of the feature maps. In a type of pooling called max-pooling, for each layer only the maximum value is passed. This enhances invariance to scale and distortions of the input. In some embodiments, the parameters of convolutional neural networks are learned by either a supervised approach and tuning the filters using a labeled training database, or an unsupervised approach. In some embodiments, methods for training a convolutional neural network for uses herein are performed using the supervised approach.

In embodiments, a pre-trained model can be used to train a convolutional neural network for uses described herein. Pre-trained models can include, for example, RGB images of tumor biopsies, monochrome images of tumor biopsies, multi-color images of tumor biopsies, multi-channel fluorescent images or mass spectrometry imagine. In embodiments, a portion of the convolutional neural network can be trained on pre-trained model.

The convolutional neural network model described herein can comprise convolutional blocks. For example, at least one, at least two, at least three, at least four, at least five, at least six, at least seven, at least eight, at least nine, at least ten or more, convolutional blocks are included in a convolutional neural network. Each block can comprise one or more convolutional layers followed by a rectified linear unit as the activation function. A weighted binary cross-entropy can be used as the loss of function to account for imbalance between the number of cancerous and non-cancerous patches. An alternative neural network platform that can be employed is a neural network architecture.

Once the deep-learning platform has been trained, out of sample predictions can be performed. Out of sample predictions involve determining the tumor margin in a tumor biopsy of interest. An exemplary convolutional neural network model process can include inputting a plurality of images of tumor margins for different types and groups of tumors. The images can be digital images, monochrome images, multi-color images, multi-channel fluorescent, or mass imaging of tumor biopsies. The convolutional neural network uses the images of tumor margins to train in recognizing tumor margins of a tumor biopsy. The training data can be subjected to a transform that can include a rotation, skewing, affine, translation, and/or mirror image. Once the convolutional neural network is trained, an image of the tumor biopsy sample can be inputted into the convolutional neural network. The convolutional neural network can identify the tumor margins of the tumor biopsy. The output is an image of the tumor margins on a computer display. The image can be a three-dimensional image of the tumor biopsy that outlines the tumor margins.

The deep-learning platform described herein determines the tumor margin relative to non-tumorous tissue based on out of sample data. The out of sample data can be images of the tumor biopsy prepared according to the methods disclosed herein (e.g., a tumor biopsy that is stained, frozen, sectioned, and fixed and stained). In embodiments, the out of sample data can be of at least 1 image of the tumor biopsy, at least 2 images of the tumor biopsy, at least 3 images of the tumor biopsy, at least 4 images of the tumor biopsy, at least 5 images of the tumor biopsy, at least 6 images of the tumor biopsy, at least 7 images of the tumor biopsy, at least 8 images of the tumor biopsy, at least 9 images of the tumor biopsy, at least 10 images of the tumor biopsy, at least 11 images of the tumor biopsy, at least 12 images of the tumor biopsy, at least 13 images of the tumor biopsy, at least 14 images of the tumor biopsy, at least 15 images of the tumor biopsy, at least 16 images of the tumor biopsy, at least 17 images of the tumor biopsy, at least 18 images of the tumor biopsy, at least 19 images of the tumor biopsy, at least 20 images of the tumor biopsy, at least 25 images of the tumor biopsy, at least 30 images of the tumor biopsy, at least 40 images of the tumor biopsy, at least 50 images of the tumor biopsy, at least 60 images of the tumor biopsy, at least 70 images of the tumor biopsy, at least 80 images of the tumor biopsy, at least 90 images of the tumor biopsy, at least 100 images of the tumor biopsy, or more images of the tumor biopsy.

Images may be in various forms, for example, SVS, TIFF, VMS, VMU, NDPI, SCN, MRXS, SVSLIDE, BIF, PDF, JPG, BMP, GIF, CZI, ZVI. BigTIFF, and any other digital format. Digital images can be located on a server or stored in the cloud. All analysis can be performed in the cloud.

The out of sample data can be based across one or more tumor biopsies. For example, the out of sample data can be based on at least 1 tumor biopsy, at least 2 tumor biopsies, at least 3 tumor biopsies, at least 4 tumor biopsies, at least 5 tumor biopsies, at least 6 tumor biopsies, at least 7 tumor biopsies, at least 8 tumor biopsies, at least 9 tumor biopsies, at least 10 tumor biopsies, at least 11 tumor biopsies, at least 12 tumor biopsies, at least 13 tumor biopsies, at least 14 tumor biopsies, at least 15 tumor biopsies, at least 16 tumor biopsies, at least 17 tumor biopsies, at least 18 tumor biopsies, at least 19 tumor biopsies, at least 20 tumor biopsies, at least 30 tumor biopsies, at least 40 tumor biopsies, at least 50 tumor biopsies, at least 60 tumor biopsies, at least 70 tumor biopsies, at least 80 tumor biopsies, at least 90 tumor biopsies, at least 100 tumor biopsies, or more. The out of sample data can be based on tumor biopsy specimens at any stage. The out of sample data can be based on tumor biopsy specimens of any grade. For example, the tumor biopsy specimen may be grade 0, grade 1, grade 2, grade 3, or grade 4. The out of sample data can be based on tumor biopsy specimens of any size. For example, at least 0.1 mm, at least 0.25 mm, at least 0.5 mm, at least 0.7 mm, at least 0.9 mm, at least 1.0 mm, at least 1.5 mm, at least 2 mm, at least 3 mm, at least 4 mm, at least 5 mm, at least 10 mm, or greater.

Once the deep-learning platform has determined the tumor margin relative to non-tumor tissue, the tumor margins from the sectioned tumor biopsy are interpolated across the tumor biopsy to determine the tumor margin. In other words, tumor margins for a three-dimensional (3-D) tumor biopsy can be reconstructed from the 2-D sectioned tumor biopsy using interpolation. Exemplary interpolation methods that can be employed in the methods described herein include piecewise constant interpolation, linear interpolation, polynomial interpolation, spline interpolation, and fractal interpolation. A preferred interpolation method is spline interpolation.

The deep-learning platform can then project the determined tumor margins onto an output operating system, such as a computer. In some cases, the computer is a portable computer such as a laptop, tablet, smartphone, and the like. The output operating system can provide a 2D image of the tumor biopsy with the tumor margins displayed. The output operating system can provide a 3D image of the tumor biopsy with the tumor margins displayed. In some instances, the 3D image can be rotated on the output operating system.

Once the tumor margin has been determined, the tumor can be removed from the tumor biopsy. The removed tumor will have a higher ratio of tumor to non-tumor tissue. The removed tumor can be used in a variety of techniques that are used for characterizing a tumor. Exemplary techniques include single-cell RNA sequencing or single-cell DNA sequencing.

It will be understood by those of skill in the art that the various programing languages (i.e. coding programs) can be used in connection with the deep-learning platform. Exemplary languages include, but are not limited to, Python, Keras, Tensorflow libraries, C, C++, CUDA, or R.

It should be understood that the various techniques described herein may be implemented in connection with hardware or software or, where appropriate, with a combination thereof. In the case of program code execution on programmable computers (e.g., the deep-learning platform), the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. The program(s) can be implemented in assembly or machine language, if desired. The language may be a compiled or interpreted language and it may be combined with hardware implementations.

5. EQUIVALENTS

It will be readily apparent to those skilled in the art that other suitable modifications and adaptions of the methods of the invention described herein are obvious and may be made using suitable equivalents without departing from the scope of the disclosure or the embodiments. Having now described certain methods in detail, the same will be more clearly understood by reference to the following examples, which are introduced for illustration only and not intended to be limiting.

6. EXAMPLES

The following are examples of methods and compositions of the invention. It is understood that various other embodiments may be practiced, given the general description provided herein.

Example 1. Tumor Sample Enrichment

Figure 2:
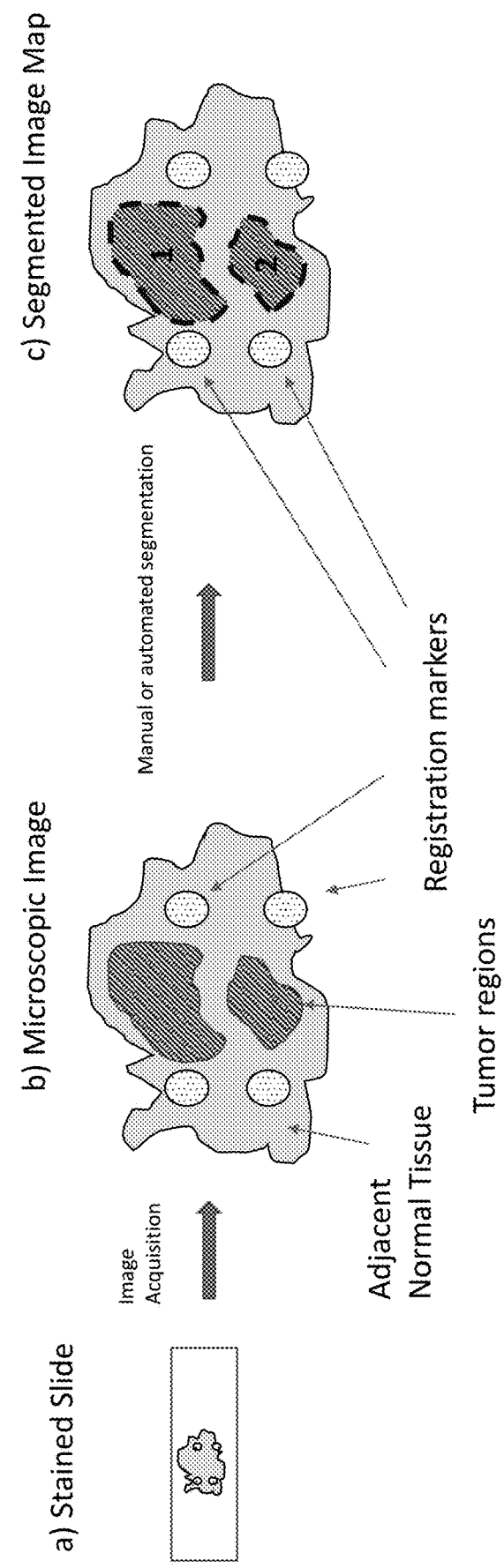
FIG. 2 is a schematic diagram depicting a tumor sample is embedded for sectioning to generate a microscopic image and a segmented image map.
Figure 3:
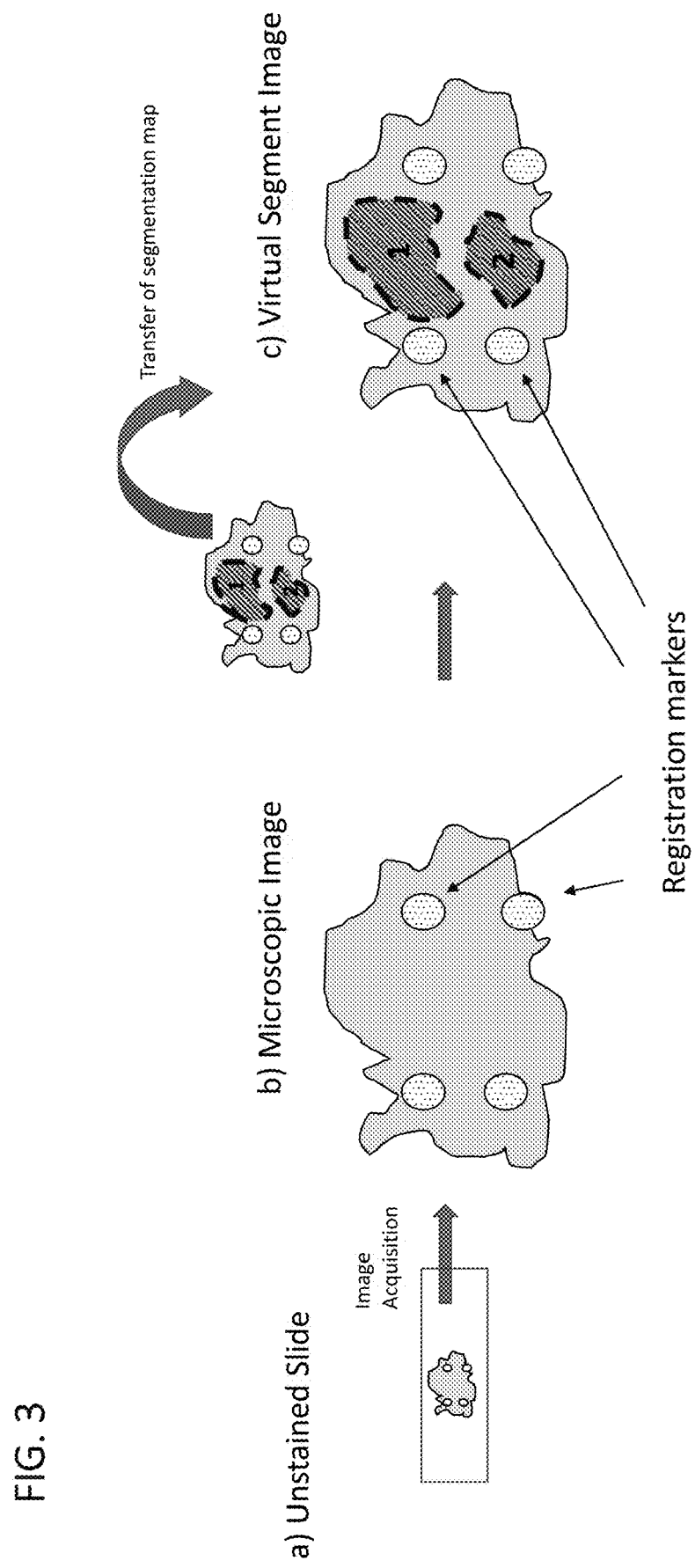
FIG. 3 is a schematic showing that the registration markers are inserted into the embedded tumor tissue.
Figure 4:
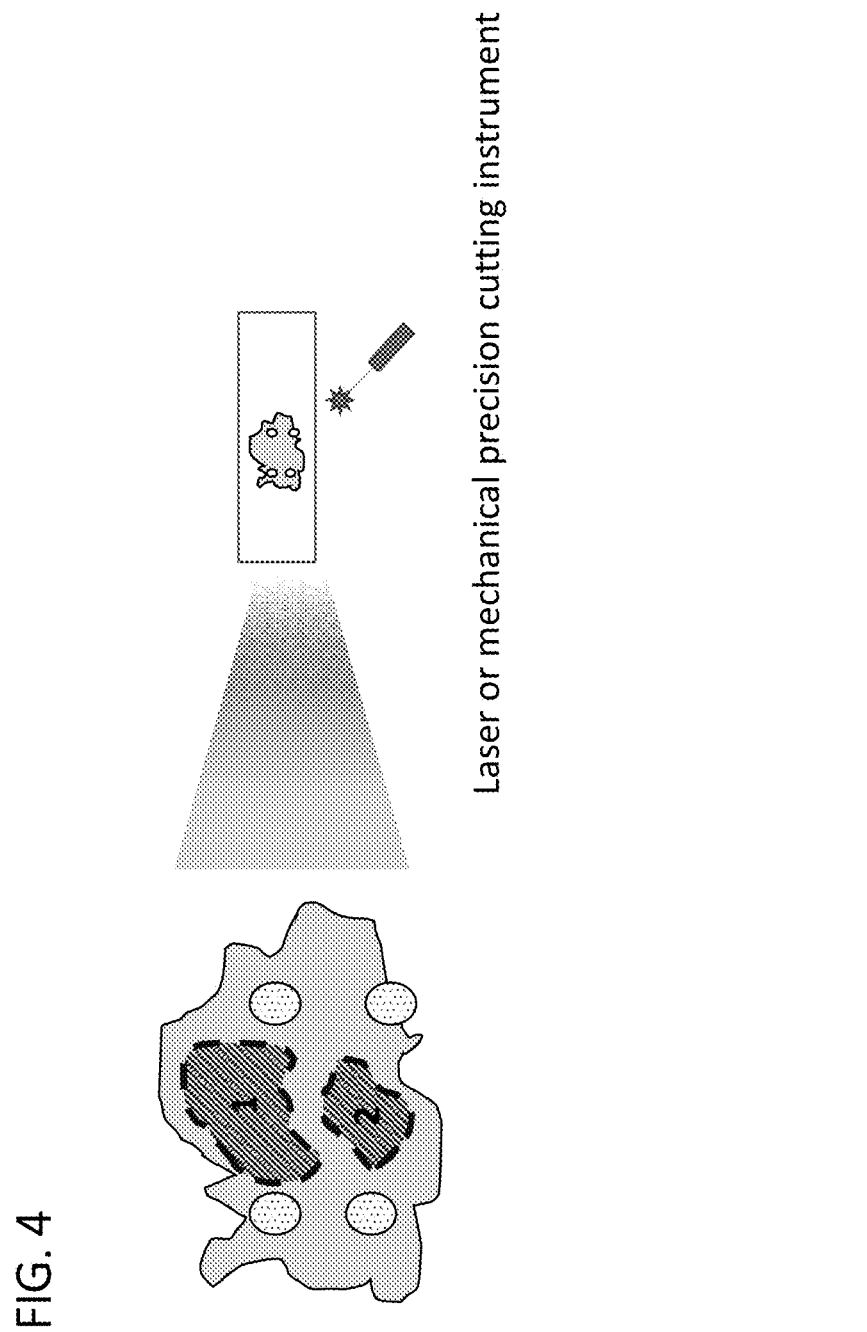
FIG. 4 is a schematic showing that serial sections of the tissue are generated using a microtome or cryptome.

The following describes an example of enriching tumor material.
Tumor Biopsy
  A surgically excised tumor, or tumor biopsy will be procured from the clinic (FIG. 1), and stored at 4° C. in adequate medium (e.g. RPMI 10% FCS, or X-VIVO serum free medium) until proceeding with embedding.
Embedding
  The tumor sample will be embedded for sectioning (FIG. 2). While Formalin fixation and paraffin embedding is applicable, embedding in a non-DNA crosslinking medium (e.g. OCT) by standard methods will be preferred.
Insertion of Registration Markers:
  Three to Four (or more) registration markers will be inserted into the embedded tumor tissue (FIG. 3). Various types of markers can be used:
    differently colored or shaped wax or plastic rods, shapes upon cross-sectioning may be round, or a combination of other shapes (square, oval, triangular).
    Injection of fluorescent dyes.
    Injection of fluorescent or colored polystyrene microspheres (e.g. Polysciences Cat-No 24287-15).
    Other tissue marking dyes (e.g. Ted Pella Inc, Cat-No 27213).
  Alternatively, the insertion of registrations markers may be performed before tissue embedding.
Sectioning of the Embedded Tissue
  Serial sections of the tissue will be generated using a microtome or cryotome (FIG. 4). Alternating sections will be generated for:
    Analytical Sections (for downstream staining and tissue segmentation). These tissue sections are preferably thick enough to allow for pathologic assessment, or computer aided segmentation, usually ~5 μm thick.
    Preparative Sections (for sample preparation/enrichment). These tissue sections are usually thicker (10, 20, 50 μm), but may be as thin as 3-5 μm. Alternatively, multiple preparative sections may be used.
  The analytical sections and the preparative sections will be is repeated until the embedded tissue sample is exhausted.
    All Analytical Sections will be mounted onto microscopic slides and numbered in order.
    All Preparative Sections will be stored in order.
Staining of Analytical Sections
  Depending on the type of embedding and type of microscopy used, the analytical sections will be stained. A colorimetric (e.g. H&E), immune-staining (IHC), fluorescent (immune-fluorescence), or immune-non-fluorescent (e.g. MIBI, DNA barcoding) staining will be used that helps to distinguish tumor vs non-tumor areas within the sample. Each of the analytical sections will be stained.
Segmentation and Registration
  Stained analytical sections will be scanned using an appropriate microscopic technique (light microscopy, fluorescent microscopy, hybridization followed by fluorescent microscopy, mass ion beam imaging).
  The microscopic image will be visualized and analyzed either by a pathologist, or by a pre-trained algorithm to identify tumor and normal areas of the tissue. Additionally, the location of the registration markers will be recorded.
  Through manual or automated image segmentation, an image map will be generated, which identifies polygonal areas of interest (e.g. tumor tissue) and boundary polygons will be generated. The coordinates of these areas and polygonal boundaries will be calculated as vectors relative to the location of the registration markers.
  This procedure will be repeated for each analytical slide and segmentation maps will be recorded for each slide.
Transfer of Segmentation Maps onto Preparative Slides
  Preparational slides will be individually micro photographed without prior staining.
  A microscopic image will be generated, primarily capturing the location of the registration markers.
  Using the spatial location of registration markers, a spatially corrected segmentation map from adjacent analytical slides will be projected on to slide coordinates, generating a virtual segmentation of the preparative slide. See, FIG. 3.
Preparation of Regions of Interest
  Based on the virtual segmentation map of the preparative slide, spatial location of each region of interest and boundary coordinates will be calculated to physical coordinates on the preparative slide. Next, using a mechanical or laser precision cutting instrument, these regions of interest will be prepared so that the tissue in these areas can be collected. See, FIG. 4. The transfer of segmentation maps onto preparative slides and preparation of regions of interest will be repeated for each preparative slide.
  All sample regions prepared will be collected and used for downstream sample preparation.

What is claimed:
1. A method for determining a tumor margin of a tumor biopsy the method comprising:
  a) preparing the tumor biopsy;
  b) optionally registering the tumor biopsy with a registration indicator;
  c) sectioning the tumor biopsy;
  d) fixing or staining the sectioned tumor biopsy;
  e) training one or more deep-learning models for a deep-learning platform using at least a validation data set, wherein the one or more deep-learning models is trained to identify the tumor margin relative to non-tumorous tissue;

f) inputting images of the sectioned tumor biopsy into the deep learning platform; and g) receiving an output of individual tumor margins of the sectioned tumor biopsy.

2. A method of removing non-tumorous tissue from a tumor biopsy using a deep-learning model comprising the steps of:

a) preparing the tumor biopsy;

b) optionally registering the tumor biopsy with a registration indicator;

c) sectioning the tumor biopsy;

d) fixing or staining the sectioned tumor biopsy;

e) inputting images of each section of the tumor biopsy into the deep-learning model, wherein the deep-learning model was trained using at least a validation data set and can identify a tumor margin relative to non-tumorous tissue, wherein the deep-learning model distinguishes tumor tissue from non-tumorous tissue;

f) interpolating the tumor margins from the tumor biopsy sections of the tumor biopsy using an interpolation method to determine the tumor margin;

g) generating the tumor margin superimposed over a rendered image of the sectioned tumor biopsy; and h) removing the non-tumorous tissue from the tumor biopsy guided by the tumor margin superimposed over the rendered image.

3. The method of claim 2, wherein the tumor biopsy has a higher ratio of tumor tissue to non-tumorous tissue.

4. The method of claim 1, wherein the tumor biopsy is a fresh tumor biopsy.

5. The method of claim 1, wherein the tumor biopsy is prepared by staining the tumor biopsy.

6. The method of claim 1, wherein the tumor biopsy is prepared by fixing the tumor biopsy.

7. The method of claim 6, wherein the tumor biopsy is fixed by freezing the tumor biopsy.

8. The method of claim 1, wherein the registration indicator is an ink.

9. The method of claim 1, wherein the registration indicator is a plurality of inks.

10. The method of claim 9, wherein the plurality of inks are each of a different color.

11. The method of claim 1, wherein the tumor biopsy is sectioned at least about twice.

12. The method of claim 1, wherein the sectioned tumor biopsy is fixed by freezing.

13. The method of claim 1, wherein the sectioned tumor biopsy is fixed with formalin.

14. The method of claim 1, wherein the sectioned tumor biopsy is stained with tissue ink.

15. The method of claim 1, wherein the sectioned tumor biopsy is stained with a plurality of tissue inks.

16. The method of claim 15, wherein the plurality of inks are each of a different color.

17. The method of claim 1, wherein the tumor biopsy is stained with hematoxylin and eosin stain.

18. The method of claim 1, wherein the deep-learning platform is a convolutional neural network.

19. The method of claim 1, wherein the deep-learning platform is an artificial neural network.

20. The method of claim 1, wherein the interpolation method is spline interpolation.

21. The method of claim 1, wherein the tumor is a melanoma or skin tumor, breast cancer tumor, ovarian cancer tumor, prostate cancer tumor, kidney cancer tumor, liver cancer tumor, gastric cancer tumor, colon cancer tumor, testicular cancer tumor, head and neck cancer tumor, pancreatic cancer tumor, brain cancer tumor, B-cell lymphoma tumor, acute myelogenous leukemia tumor, chronic myelogenous leukemia tumor, chronic lymphocytic leukemia tumor, T cell lymphocytic leukemia tumor, bladder cancer tumor, or lung cancer tumor.

22. The method of claim 21, wherein the tumor is selected from the group consisting of a melanoma tumor, breast cancer tumor, lung cancer tumor, and bladder cancer tumor.

23. The method of claim 2, wherein the tumor biopsy with non-tumorous tissue removed is used for single-cell RNA sequencing or singe-cell DNA sequencing.

* * * * *